United States Patent [19]

Jackson et al.

[11] Patent Number: 5,449,509
[45] Date of Patent: Sep. 12, 1995

[54] DESENSITISING DENTRIFRICE

[75] Inventors: Robert J. Jackson; Susan A. Duke; Mark A. Wicks, all of Weybridge, England

[73] Assignee: Beecham Group p.l.c., England

[21] Appl. No.: 33,991

[22] Filed: Mar. 19, 1993

Related U.S. Application Data

[60] Continuation of Ser. No. 908,434, Jun. 29, 1992, abandoned, which is a continuation of Ser. No. 701,666, May 16, 1991, abandoned, which is a division of Ser. No. 499,658, Mar. 27, 1990, Pat. No. 5,087,444.

[30] Foreign Application Priority Data

Mar. 28, 1989 [GB] United Kingdom ............... 89069140

[51] Int. Cl.$^6$ ............................................. A61K 7/16
[52] U.S. Cl. ...................................................... 424/49
[58] Field of Search ...................................... 424/49–58

[56] References Cited

U.S. PATENT DOCUMENTS

| | | | |
|---|---|---|---|
| 3,122,483 | 2/1964 | Rosenthal | 167/93 |
| 3,689,636 | 9/1972 | Svajda | 424/49 |
| 3,699,221 | 10/1972 | Schole et al. | 424/54 |
| 3,863,006 | 1/1975 | Hodosh | 424/49 |
| 3,988,434 | 10/1976 | Schole et al. | 424/54 |
| 4,283,385 | 8/1981 | Dhabhar et al. | 424/52 |
| 4,357,318 | 11/1982 | Shah et al. | 424/52 |
| 4,751,072 | 6/1988 | Kim | 424/49 |
| 4,933,171 | 6/1990 | Bristow et al. | 424/57 |
| 5,015,465 | 5/1991 | Stran | 424/52 |
| 5,087,444 | 2/1992 | Jackson et al. | 424/49 |

*Primary Examiner*—Shep K. Rose
*Attorney, Agent, or Firm*—Rosenman & Colin

[57] ABSTRACT

An oral hygiene composition for use in the treatment of dentine hypersensitivity comprises a water soluble strontium salt and a water soluble potassium salt, together with a dentally acceptable excipient. Preferably, the composition is in the form of a dentifrice comprising an abrasive silica and a thickening silica, and optionally includes an ionic fluorine-containing compound.

11 Claims, 2 Drawing Sheets

DESENSITISING DENTRIFRICE

This application is a continuation application of U.S. Ser. No. 07/908,434, filed Jun. 29, 1992, now abandoned; which was a continuation application of U.S. Ser. No. 07/701,666, filed May 16, 1991, now abandoned; which was a division of U.S. Ser. No. 07/499,658, filed Mar. 27, 1990, now U.S. Pat. No. 5,087,444, issued Feb. 11, 1992; with a claimed priority from Great Britain application 89069140, with a priority date of 28 Mar. 1989.

The present invention relates to oral hygiene compositions, and in particular to compositions for the treatment of dentine hypersensitivity.

Many compositions have been proposed for the treatment of dentine hypersensitivity, for instance compositions comprising as the active agent formaldehyde, sodium or stannous fluoride, zinc chloride, silver nitrate, sodium citrate/citric acid (U.S. Pat. No. 4,011,309, Lutz H. J., to Marion Laboratories, Inc), strontium salts (U.S. Pat. No. 3,122,483, Rosenthal M. W., to Block Drug Company, U.S. Pat. No. 4,367,219, Schole M. L., EP O 200 323, Leigh P. L., to Beecham Group p.l.c.), potassium and other alkali metal nitrates (U.K. 1 466 930, Hodosh, M.) and other potassium salts (EP O 095 871, Reckitt and Colman, PCT/U.S. Pat. No. 85/00123, The Trustees of Columbia University in the City of New York, and U.K. application No. 87 06187, to Unilever plc). In addition, an application (EP O 346 957, to Unilever plc) published after the priority date of the present application discloses a tooth desensitising oral composition comprising a finely divided hydroxyapatite in combination with a source of potassium and/or strontium ions. Whilst hydroxyapatite is known as an abrasive, the use thereof with strontium or potassium had been previously unreported.

We have now discovered that particularly effective anti-sensitivity activity can be achieved by a particular combination of anti-sensitivity agents.

BRIEF DESCRIPTION OF THE DRAWINGS

The present invention is more fully described in the following discussion and drawings in which.

Figure 1:
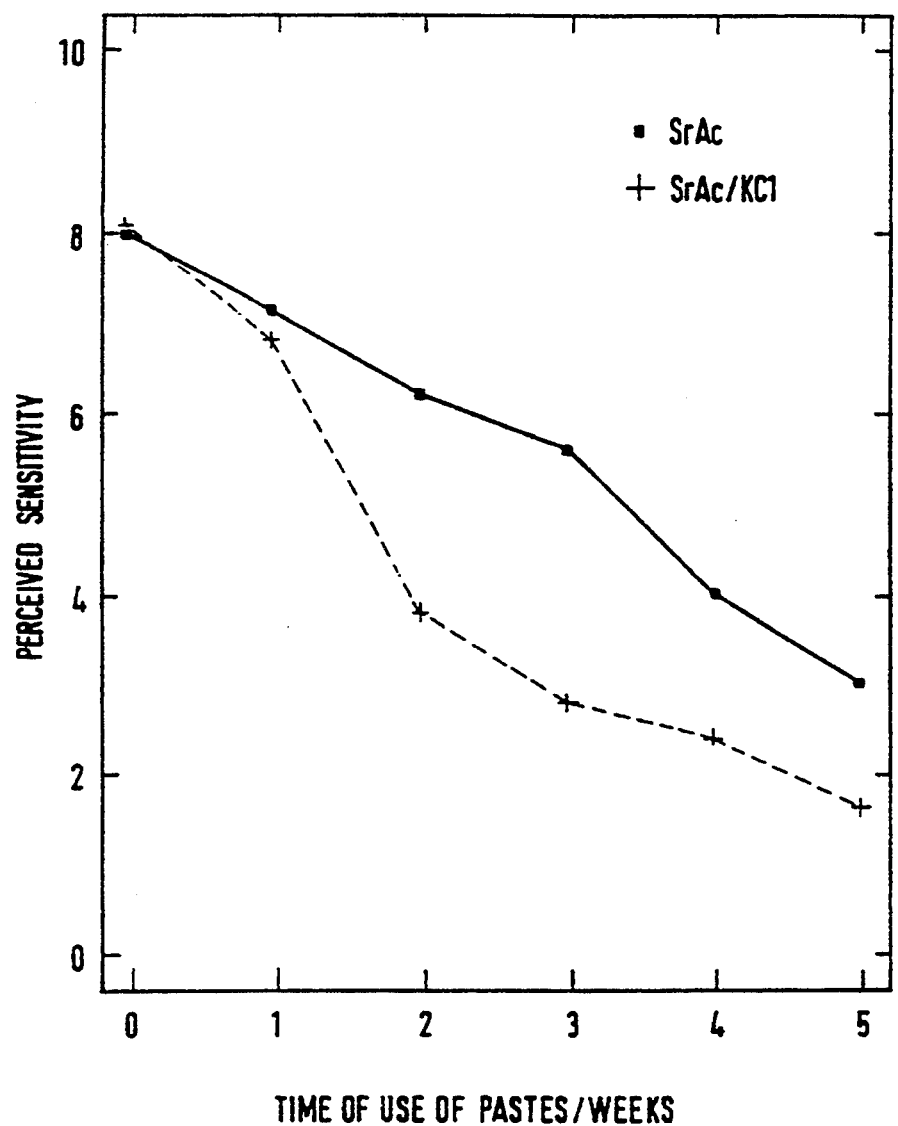
FIG. 1 is a comparative graph showing the sensitivity effect of a toothpaste having SrAC, without and with the KCl of the present invention on reaction with ethyl chloride.

Accordingly, the present invention provides an oral hygiene composition comprising:
(i) a water soluble, non-toxic, strontium salt;
(ii) a water soluble, non-toxic, potassium salt; and
(iii) a dentally acceptable excipient.

It will be appreciated that the present invention does not extend to any composition which has been prior disclosed by EP-A-0 346 957 or an equivalent thereof.

Suitable strontium salts include strontium chloride, strontium bromide, strontium iodide, strontium acetate, strontium edetate, strontium nitrate, strontium salicylate and strontium lactate, of which strontium acetate is especially preferred. It is advantageous to use strontium acetate in the form of the hemihydrate. Typically the strontium salt is present in a range to provide from 0.1 to 15%, preferably 1 to 10%, more preferably 2 to 8%, by weight of the composition as strontium ions.

Suitable potassium salts include potassium chloride, potassium bromide, potassium iodide, potassium acetate, potassium citrate, potassium nitrate and potassium lactate, of which potassium chloride or potassium acetate especially preferred. Typically the potassium salt is present in a range to provide from 0.1 to 15%, preferably 0.25 to 15%, more preferably 0.5 to 10%, by weight of the composition as potassium ions.

It will be appreciated that the potassium salt should be selected such that the anions thereof are compatible in aqueous solution with strontium ions.

Suitably, the ratio of the potassium salt to the strontium salt will be in the range of from 10:1 to 1:10, preferably 5:1 to 1:5, by weight of the respective ions.

The dentally acceptable excipient in compositions of the invention will include any of the well known ingredients conventionaly used in oral hygiene compositions, provided that they are compatible with strontium ions in aqueous solution.

In a further aspect of the invention, compositions may also comprise an ionic fluorine-containing compound, to provide an additional anti-caries effect.

The ionic fluorine-containing compound may be a fluoride salt, preferably an alkali metal fluoride. Sodium fluoride is especially preferred but the corresponding potassium and/or lithium salts can also be employed. Other suitable fluoride salts include ammonium fluoride, tin (II) fluoride and zinc fluoride.

In addition to, or instead of, the above fluoride salts, the ionic fluorine-containing compound may also comprise a monofluorophosphate, preferably an alkali metal monofluorophosphate. Sodium monofluorophosphate is especially preferred but the corresponding potassium and/or lithium salts may also be employed. Other suitable monofluorophosphates include monofluoropolyphosphate salts, for instance compounds of the formulae $Na_4P_3O_9F$, $K_4P_3O_9F$, $Na_3KP_3O_9F$, $Na_3KP_3O_9F$ $(NH_4)_3NaP_3O_9F$, and $Li_4P_3O_9F$.

The total amount of fluoride and/or monofluorophosphate used is to some extent dependent on the type of oral hygiene composition, but it should be an effective, but non-toxic, amount.

Typically the ionic fluorine-containing compound(s) is present in an amount to provide a total of from 0.01 to 0.25% of fluorine, preferably 0.025 to 0.15%, based on the weight of the composition.

A composition of the invention may optionally contain other agents known to enhance the anticaries effect of fluoride and monofluorophosphate, for instance, calcium glycerophosphate (which is known to enhance the anticaries activity of monofluorophosphate) which may be incorporated in a weight ratio of up to 1:3, preferably 1:20 to 1:3, compared to the total weight of monofluorophosphate.

A composition of the invention is preferably presented in the form of a dentifrice, for instance a toothpaste or dental powder formulation. A composition may also be in the form of another oral hygiene composition, for example, the ingredients may be incorporated into a mouthwash which may be of the suspension variety or into a composition which will be chewed by the user, for example, chewing gum, tablets, pastilles and lozenges.

When the oral hygiene composition is in the form of a dentifrice, the composition will also comprise an abrasive. The abrasive may be any abrasive that is compatible with the strontium salt, that is one which will not render strontium ions inactive, for example by causing strontium ions to be lost from solution by the formation of an insoluble strontium salt. Compatible abrasives suitable for use in the present invention include, for example, silica, alumina, aluminium hydroxide, insoluble sodium metaphosphate, strontium carbonate, strontium phosphates, pumice, hydroxyapatite, plastics particles or mixtures thereof.

In one aspect of the invention, there is provided an oral hygiene composition which does not comprise hydroxyapatite.

The abrasive is typically present in the range from 5 to 75% preferably 5 to 50%, by weight of the composition.

Preferably the abrasive is silica which may be a natural amorphous silica, for instance, diatomaceous earth, or a synthetic amorphous silica, for instance a precipitated silica or a silica gel, such as the silica xerogels described in U.S. Pat. No. 3,538,230.

Preferred precipitated silicas are those marketed under the trade marks 'Zeodent' and 'Tioxosil' by J. M. Huber Corporation and Rhone-Poulenc, respectively.

The coformulation of a strontium salt and an ionic-fluorine containing compound is recognised to present a problem due to the formation of, for instance, insoluble strontium fluoride or insoluble strontium monofluorophosphate.

It has been found that in compositions of the present invention, further comprising an ionic fluorine-containing compound, this problem may be overcome by the inclusion of a silica, by analogy with the disclosure of EP-A-O 200 323 (to Beecham Group p.l.c.).

Accordingly, in a further aspect of the invention, there is provided an oral hygiene composition, as hereinbefore defined, comprising an ionic fluorine-containing compound, as hereinbefore defined, and silica which may be a thickening silica or an abrasive silica or a combination thereof and optionally comprising an additional non-silica abrasive.

Preferably, an abrasive silica, as hereinbefore defined, is used in combination with a thickening silica, with suitable amounts thereof being in the weight ranges of from 5 to 20% (abrasive silica) and from 3 to 12% (thickening silica), by weight of the composition.

Alternatively, in the absence of a silica abrasive, a thickening silica may suitably be used in from 1 to 15% by weight of the composition.

Preferred thickening silicas include the products marketed under the trade marks 'Sipernat' and 'Syloid' by Degussa and by W. R. Grace, respectively.

The compositions of the invention will also usually contain as excipients surfactants, humectants, gelling agents, and other ingredients such as flavouring, sweetening and colouring agents.

Surfactants used in the composition of the invention are normally water-soluble, non-soap, or synthetic organic detergents. Particularly preferred surfactants are low ionic materials such as for example sodium N-methyl-N-cocoyl taurate, which is marketed under the trade name 'Adinol CT' by Croda or non-ionic materials such as for example condensates of propylene glycol and polyethoxylated hydrogenated castor oil, for instance, cremaphors. Other suitable surfactants include the water-soluble salts of: higher fatty acid monoglyceride monosulphates (for example sodium hydrogenated coconut fatty acid monoglyceride monosulphate); higher alkyl sulphates (for example sodium lauryl sulphate); alkylarylsulphonates (for example sodium dodecylbenzenesulphonates); and higher alkyl sulphoacetates (for instance sodium lauryl sulphoacetate). There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amides of glycine, sarcosine, alanine, 3-aminopropanoic acid and valine, particularly the N-lauroyl, myristoyl and palmitoyl sarcosinate compounds.

The surfactants are generally present in an amount of 0.05 to 15%, preferably 0.05 to 5% by weight of composition.

Humectants suitable for use in compositions of the invention include, for example, glycerine, sorbitol and/or a glycol, including suitable mixtures thereof. Suitably, the glycol is propylene glycol or a polyethylene glycol.

It is also preferred to use in those compositions of the invention which are toothpastes a gelling agent such as a natural or synthetic gum or gum-like material. Whilst non-ionic gums such as guar gum or xanthan gum are particularly preferred, other gums or gum-like materials, such as, for example, Irish Moss, gum tragacanth, sodium carboxymethylcellulose, polyvinylpyrrolidone, starch or a thickening silica may also be used. The gelling agent content is usually from 0.001 to 10%, preferably 0.01 to 5% by weight of the composition.

Other materials may be added such as for example sweetening agents (e.g. soluble saccharin), flavouring oils (e.g. oils of spearmint, wintergreen peppermint), menthol, chloroform, colouring or whitening agents (e.g. titanium dioxide), preservative (e.g. sodium benzoate), emulsifying agents, silicones, alcohol, chlorophyll compounds (e.g. sodium copper chlorophyllin), antibacterial agents (e.g. triclosan, chlorhexidine), antiplaque agents and anti-calculus agents.

If necessary and required, compositions of the invention may include water.

The pH of compositions according to the invention will be dentally acceptable, and typically in the range pH 5 to 9.

Oral hygiene compositions according to the invention may be prepared by mixing the ingredients thereof in the required proportions in any order that is convenient and thereafter and if necessary adjusting the pH.

Mouth-washes according to the invention may be presented for use as a conventional gargle or may be packaged in a suitable delivery device for use as a mouth spray.

The invention also provides a method of treating dentine hypersensitivity which method comprises the application of an effective amount of a composition according to the invention to the oral cavity.

This invention will now be illustrated with reference to the following Examples.

|  | % |
| --- | --- |
| Example I - Toothpasste |  |
| Sorbitol (70% solution) | 33.0 |
| Saccharin (30% solution) | 1.0 |
| Xanthan gum | 1.0 |
| Glycerin | 11.0 |
| Titanium dioxide | 1.0 |
| Thickening silica | 6.5 |
| Abrasive silica | 14.0 |

| | % |
|---|---|
| Strontium acetate | 8.0 |
| Potassium acetate | 4.9 |
| Sodium N-methyl-N-cocoyl laurate | 2.0 |
| Preservatives | 0.1 |
| Flavour | 1.0 |
| Water | to 100.0 |
| Example 2 - Mouthwash | |
| Potassium acetate | 1.22 |
| Strontium acetate | 2.00 |
| Ethanol | 10.00 |
| Glycerin | 5.00 |
| Flavour | 0.12 |
| Hydrogenated castor oil derivative* | 0.20 |
| Sodium saccharin | 0.05 |
| Soluble dyes | q.s. |
| Deionized water | to 100.00 |

*Condensate of propylene glycol with polyethoxylated hydrogenated caster oil

DATA

Introduction

The ability of a dentifrice according to the invention comprising strontium acetate (8%), potassium chloride (3.75%) and sodium fluoride (0.22%) to alleviate dentine hypersensitivity was compared with that of a dentifrice comprising strontium acetate (8%) and sodium fluoride (0.22%).

Method

Subjects (n=5) were initially assessed for sensitivity by exposing a sensitive tooth to cold air and to ethyl chloride stimulation. A subjective assessment was made on the scale 0 to 10 (0 being no pain at all, 10 being extremely painful).

The appropriate dentifrice was assigned to each subject to use for a period of five weeks and further assessments of sensitivity were made at weekly intervals.

Figure 2:
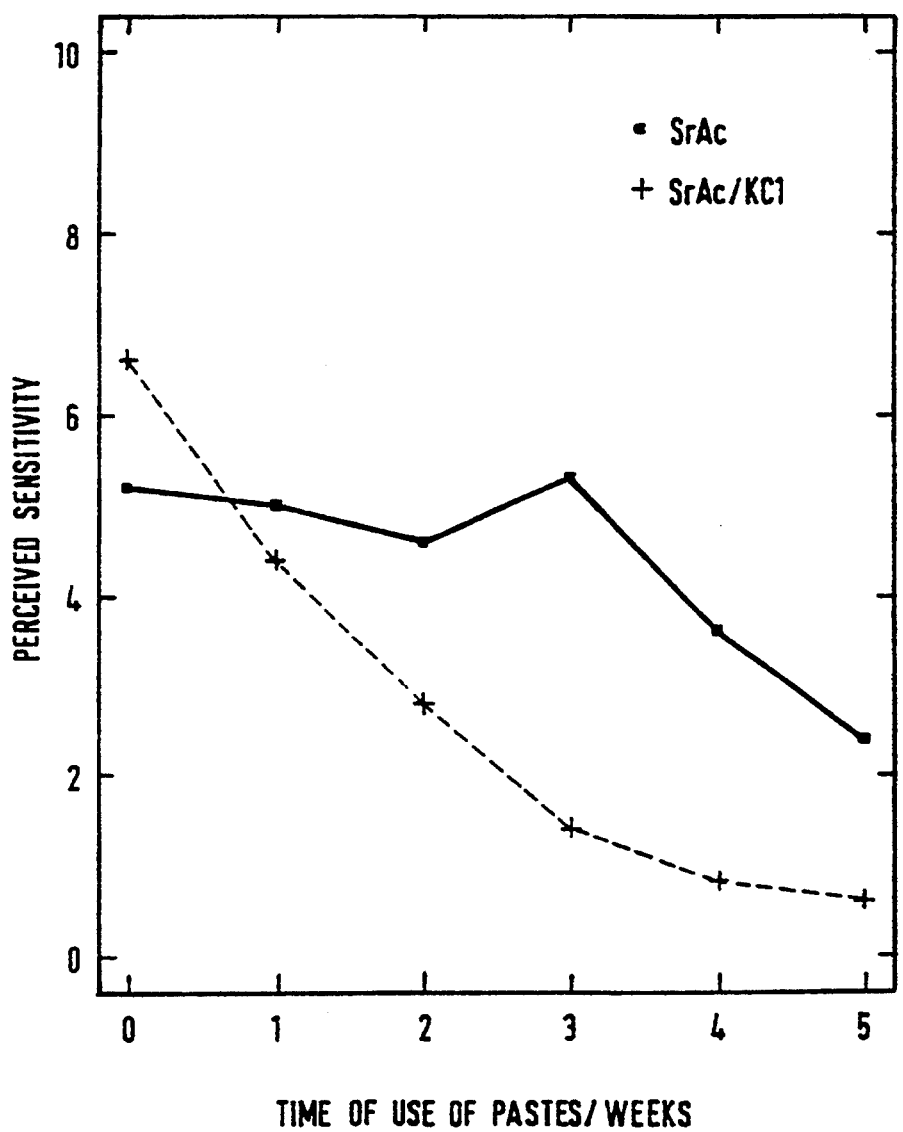
FIG. 2 is a comparative graph showing the sensitivity effect of a toothpaste having SrAc, without and with the KCl of the present invention on reaction with cold air.

The results are presented in FIGS. 1 and 2 (SrAc being strontium acetate).

Results

FIG. 1—Ethyl chloride stimulation
SrAc/KCl/NaF superior to SrAc/NaF
$p<0.001$ at 2, 3, 4 and 5 weeks use of dentifrices.
FIG. 2—Air Blast stimulation
SrAc/KCl/NaF superior to SrAc/NaF
$p<0.01$ at 4 weeks use of dentifrices
$p<0.05$ at 3 and 5 weeks use of dentifrices

Conclusion

FIGS. 1 and 2 show quite clearly that, in response to either ethyl chloride or air blast stimulation, a strontium acetate/potassium chloride/sodium fluoride dentifrice is statistically superior to a similar dentifrice in which potassium chloride is omitted.

I claim:

1. An oral hygiene non-fluoride toothpaste composition comprising:
   (i) 0.1% to 15% by weight of a water soluble, non-toxic, strontium salt selected from the group consisting of strontium chloride, strontium bromide, strontium iodide, strontium acetate, strontium edetate, strontium nitrate, strontium salicylate and strontium lactate, effective for the treatment of dentine hypersensitivity;
   (ii) 0.1% to 15% by weight of a water soluble, non-toxic, potassium salt compatible in aqueous solution with strontium ions selected from the group consisting of potassium chloride, potassium bromide, potassium iodide, potassium acetate, potassium citrate, potassium nitrate, and potassium lactate, effective for the treatment of dentine hypersensitivity; and
   (iii) a dentally acceptable excipient wherein the pH of the composition is dentally acceptable and in the range pH 5 to 9 and the composition further comprises an abrasive of silica, wherein the ratio of said potassium salt to said strontium salt is in the range of from 10:1 to 1:10.

2. A composition according to claim 1 wherein the potassium salt is potassium acetate or potassium chloride.

3. A composition according to claim 1 wherein an abrasive is present in the range from 5 to 75% by weight of the composition.

4. An oral hygiene composition according to claim 1 further comprising a thickening silica.

5. A composition according to claim 4 wherein the thickening silica is present in from 1 to 15% by weight of the composition.

6. A composition according to claim 1 comprising a combination of an abrasive silica and a thickening silica, present in from 5 to 20% and from 3 to 12% by weight of the composition respectively.

7. A composition according to claim 1 comprising a surfactant which is a non-ionic or a low ionic material.

8. A composition according to claim 1 wherein the strontium salt is strontium acetate.

9. A method of treating dentine hypersensitivity which method comprises the application of an effective amount of a composition as defined in claim 1 to the oral cavity.

10. An oral hygiene non-fluoride toothpaste composition comprising:
    (i) 0.1% to 15% by weight of strontium acetate;
    (ii) 0.1% to 15% by weight of potassium nitrate; and
    (iii) a dentally acceptable excipient wherein the pH of the composition is dentally acceptable and in the range pH 5 to 9 and the composition further comprises an abrasive of silica, wherein the ratio of said potassium salt to said strontium salt is in the range of from 10:1 to 1:10.

11. The composition according to claim 1, wherein said abrasive is a silica abrasive, and wherein said composition comprises a thickening silica.

* * * * *